United States Patent [19]

La Rosa

[11] Patent Number: 5,480,379
[45] Date of Patent: Jan. 2, 1996

[54] ULTRASONIC DISSECTOR AND DETACHER FOR ATHEROSCLEROTIC PLAQUE AND METHOD OF USING SAME

[76] Inventor: Antonio La Rosa, Via Toledina, 2, 27026 Garlasco, Pavia, Italy

[21] Appl. No.: 130,879

[22] Filed: Oct. 4, 1993

Related U.S. Application Data

[63] Continuation-in-part of Ser. No. 882,976, May 14, 1992, abandoned.

[30] Foreign Application Priority Data

May 22, 1991 [IT] Italy ................................ MI91A1415
Jun. 6, 1993 [EP] European Pat. Off. .............. 93108759

[51] Int. Cl.⁶ .................................................. A61B 17/20
[52] U.S. Cl. ........................... 604/22; 606/171; 606/159
[58] Field of Search .............................. 604/22; 606/127, 606/128, 159, 169, 171; 607/97; 601/2; 128/662.06

[56] References Cited

U.S. PATENT DOCUMENTS

| | | | |
|---|---|---|---|
| 3,086,288 | 4/1963 | Balamuth et al. . | |
| 3,433,226 | 3/1969 | Boyd . | |
| 3,526,219 | 9/1970 | Balamuth | 128/2 |
| 3,565,062 | 2/1971 | Kuris | 606/159 |
| 3,730,185 | 5/1973 | Cook et al. | 606/159 |
| 3,809,093 | 5/1974 | Abraham . | |
| 3,990,452 | 11/1976 | Murry et al. . | |
| 4,515,583 | 5/1985 | Sorich | 604/22 |
| 4,559,927 | 12/1985 | Chin | 606/159 |
| 4,594,996 | 6/1986 | Ibrahim et al. | 606/159 |
| 4,804,364 | 2/1989 | Dieras et al. | 604/22 |
| 4,832,683 | 5/1989 | Idemoto et al. . | |
| 4,870,953 | 10/1989 | DonMichael et al. | 128/24 A |
| 4,886,491 | 12/1989 | Parisi et al. . | |
| 4,962,755 | 10/1990 | King et al. | 604/22 X |
| 5,062,827 | 11/1991 | Wiksell . | |

FOREIGN PATENT DOCUMENTS

| | | |
|---|---|---|
| 340572 | 12/1977 | Austria . |
| 238667 | 9/1987 | European Pat. Off. . |
| 2176110 | 12/1986 | United Kingdom . |
| WO90/01300 | 2/1990 | WIPO . |

OTHER PUBLICATIONS

M. K. O'Malley, "Intimal Hyperplasia", Vasc Surg 6, 343–345, Jul., 1992.
Alexander W. Clowes, MD et al, "Prevention of stenosis after vascular reconstruction: Pharmacologic control of initimal hyperplasia—A review", Journal of Vascular Surgery, vol. 13, No. 6 pp. 885–891.

*Primary Examiner*—C. Fred Rosenbaum
*Assistant Examiner*—Frank Wilkens, III
*Attorney, Agent, or Firm*—Oliff & Berridge

[57] ABSTRACT

An apparatus for removing atherosclerotic plaque includes a probe attachable to an ultrasound transducer and a catheter surrounding a transmission part of the probe for conveying liquid to the working part of the probe. Preferably, the catheter is made from a material having a negligible coefficient of friction relative to the liquid so that oscillation of the probe is not damped by surrounding tissue or by the catheter. The catheter is arranged so that the liquid wets the entire working part of the probe even when the working part is extended deep inside a vessel.

26 Claims, 7 Drawing Sheets

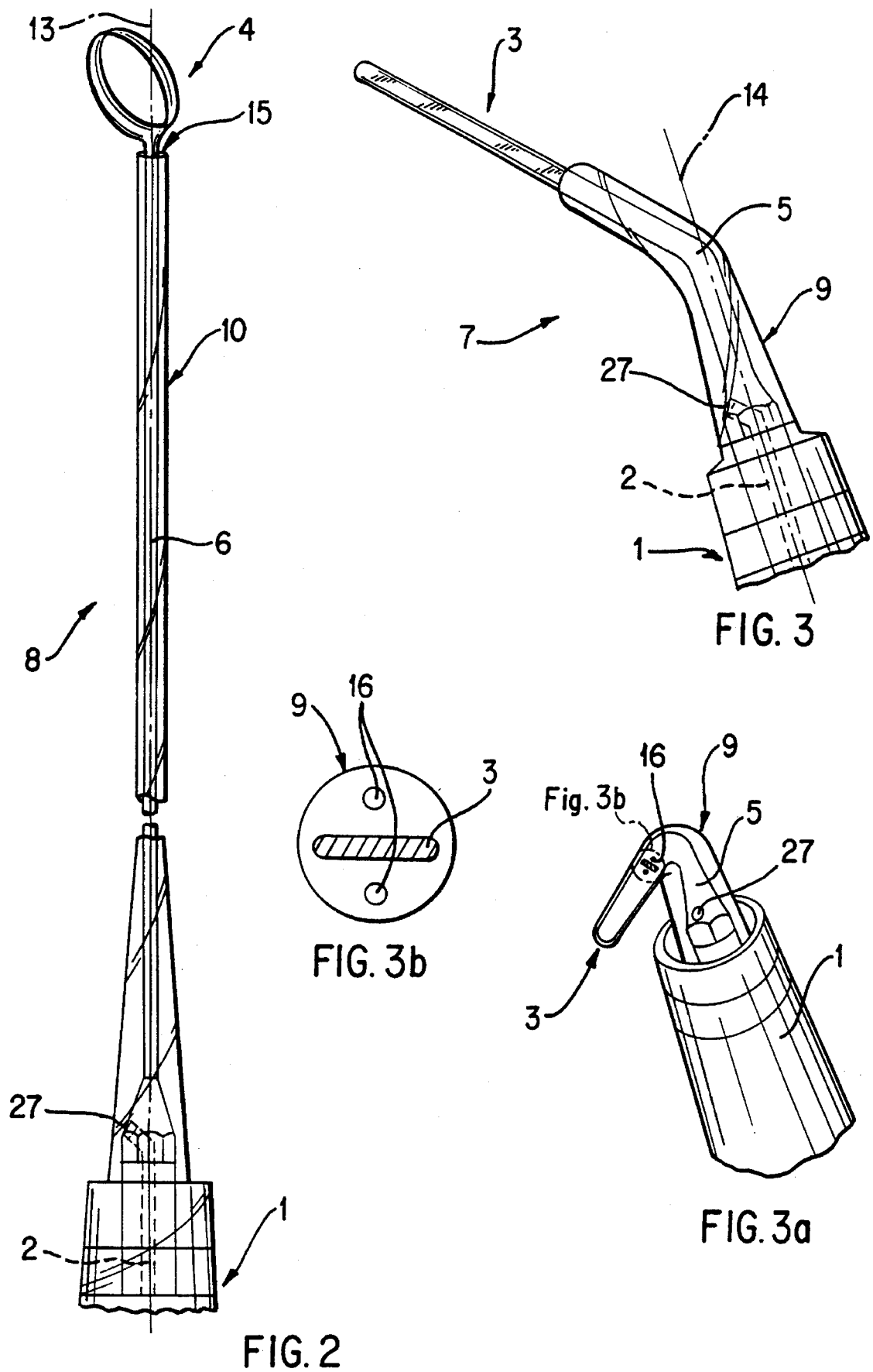

ULTRASONIC DISSECTOR AND DETACHER FOR ATHEROSCLEROTIC PLAQUE AND METHOD OF USING SAME

This is a Continuation-In-Part of U.S. patent application Ser. No. 07/882,976, filed May 14, 1992, now abandoned by Antonio La Rosa, entitled "Ultrasonic Dissector and Detacher for Atherosclerotic Plaques", the disclosure of which is incorporated herein by reference in its entirety. The disclosure of European Patent Application No. 93108759.7, filed Jun. 6, 1993, by Antonio La Rosa also is incorporated herein by reference in its entirety.

BACKGROUND OF THE INVENTION

1. Field of the Invention

The invention relates to apparatus and methods for removing atherosclerotic plaque from vessels.

2. Description of Related Art

The removal of arterial obturations or occlusions which are due to the formation of atherosclerotic plaque with the aid of ultrasound is one of several, commonly used methods.

In classical endarterectomy, the thrombus located at the occlusion site of the artery, including the inner wall of the artery adhering to the thrombus, the intima and optionally also the media, is removed. This is carried out either as a so-called "open endarterectomy," in which the artery is opened along its length, or as a so-called "semi-open endarterectomy," which starts from two cross-sections in the artery, and removes material by means of so-called ring strippers. Although the open endarterectomy has the advantage that removal of the thrombus can be visually monitored, the sutures of the restored artery are a possible cause of stenoses. In this semi-open endarterectomy, on the other hand, the problem is that—in particular with long obstructions—the mechanical removal by means of a stripper often results in irregular surfaces of the inner walls of the arteries. However, if the media has been only partially removed, or if it was injured, this generally leads to postoperative hyperplasias.

In the case of angioplasty, occluded arteries are expanded with the aid of a balloon-tipped catheter. However, this treatment, which is often performed as a preparatory or additional measure for angioplasty, is to a certain extent always traumatizing. Secondary stenoses due to miointimal hyperplasias are a consequence of this procedure.

Relatively extensive plaques are also removed with the aid of lasers. There is a risk, however, of thermal irritation or injury to the inner walls of the vessel, and perforation of the vessel is also possible.

The use of ultrasound for removing atherosclerotic plaques also has been proposed, for example in U.S. Pat. No. 3,565,062, which describes a hollow, vibrating probe, a catheter coordinated with this probe and provided with slots taking up plaque strips cut from the inner wall of the vessel. U.S. Pat. No. 3,526,219 describes the removal of tissue parts, the ultrasonic energy being used for dividing the tissue into very small parts ("micro-chopping"), which can then be extracted. In both cases—as already stated in U.S. Pat. No. 4,870,953 regarding the method described in U.S. Pat. No. 3,526,219—traumatizing effects on the media may occur on the one hand and, on the other hand, there is uncertainty about the actual size of the removed occlusions.

U.S. Pat. No. 4,962,755 describes a method in which a short, curved ultrasonic probe is introduced into an incision in the artery. Liquid is fed to the vibrating working part of the probe via a small, rigid tube arranged parallel to the probe. Since, on the one hand, the vibrating working part comes to rest between removed plaque or media and adventitia and, on the other hand, on further insertion into the artery, the liquid-providing tube is not pushed into this space, wetting of the vibrating working part takes place only on one side, and wetting is possible only to a limited extent. Thus, after loosening of the plaque, it is necessary to remove the plaque by means of forceps from an incision made in the middle of the occlusion or from two distal or proximal incisions. It is evident that such a method can be successful only in the case of occlusions covering a small area, since otherwise removal of the plaque, which may be only partially detached, by means of forceps can result in the plaque being torn off from the media, or plaque being torn and thus only incompletely removed. Traumatizing of the media cannot be ruled out.

Here too, the problem of satisfactory dissection of the "end-point" is not solved. This problem, which was impossible to solve satisfactorily in the classical endarterectomy, consists in the fact that the transition between the treated inner wall of the artery and that region of the inner wall of the artery in which untreated intima and media remain must be homogeneous and regular, since otherwise this is one of the possible causes of postoperative thromboses.

Austrian Patent No. 340,572 describes ultrasonic probes that are intended for the removal of both small-area and extensive plaques. In the case of the short, bent probe, which is similar to that described in U.S. Pat. No. 4,962,755, the liquid, as one of two alternative possibilities described, is passed via a channel provided in the interior of the probe, through outlet orifices provided at the transition point to the inclined part of the probe, to the vibrating working part of the probe. However, since the working part vibrates transversely, the liquid will not be able to reach the end of the working part but will be sprayed off beforehand. In the case of the long probe too, which is in the form of a ring stripper, the liquid—once again as one of two alternative possibilities—is passed via a channel provided in the probe to the transversely vibrating ring. Apart from the fact that wetting of the ring is once again insufficient, the efficiency of the long probe is increasingly reduced during its insertion into the interior of the artery because the long rod carrying the transversely vibrating ring and having an internal channel moves forward in the narrow intermediate space between adventitia and detached plaque or detached media. The inner wall of the vessel and the detached layers thus exert on the longitudinally vibrating rod a pressure that results in a significant decline in the efficiency of the probe. Finally, since nodes are formed, the transverse vibrations of the ring cease.

SUMMARY OF THE INVENTION

Accordingly, it is an object of the invention to provide an apparatus that permits the removal of atherosclerotic plaque and the media, independently of the degree of the atherosclerotic impairment thereof. With the artery closed apart from a small incision, traumatizing effects on the remaining vessel wall are avoided.

In order to achieve the above and other objects, and to overcome the shortcomings set forth above, an apparatus for the removal of atherosclerotic plaque includes a probe that is attachable to an ultrasound transducer, and a catheter surrounding a transmission part of the probe for conveying liquid to the working part of the probe. Preferably the catheter is made from a material having a negligible coefficient of friction relative to the liquid so that oscillation of the transmission part, and thus of the working part, of the probe is not damped by surrounding tissue or by the catheter. The working part of the probe preferably extends from the transmission part of the probe at an angle between 0° and 90°. In such an arrangement, the transmission part oscillates in a direction parallel to its axis, while the working part oscillates at least partly transversely. The working part can be spatula-shaped or ring-shaped, for example.

In a method of removing atherosclerotic plaque according to the invention, a probe having the spatula-shaped working part is used to separate the media from the adventitia adjacent to end points of a length of vessel containing plaque. These end points are located beyond the plaque-containing portion of the vessel, that is, at healthy portions of the vessel. At each end point, an incision is made in the vessel wall; the spatula probe is inserted to separate a small portion of the media from the adventitia; a small cut is made in the separated media using, for example, forceps; and then the spatula probe is used to extend the small incision entirely around the circumference of the media so that the portion of the media that does not contain plaque is separated cleanly from the portion of the media containing plaque. When the plaque extends over a short length of vessel, as is common, for example, in the carotid arteries, the spatula probe can be used to separate the media (and thus the plaque on the media) from the adventitia between the two endpoints. When the plaque extends over a long distance, as is common, for example, in the femoral arteries, the ring probe preferably is used to separate the media (and the attached plaque) from the adventitia between the two endpoints. The plaque-containing media, thus separated from the adventitia, can then be grasped and withdrawn from the vessel through one of the endpoint incisions.

The effectiveness of the probe—essentially due to the occurrence of cavitation—with complete detachment of the media (and of the plaque) from the adventitia is improved by virtue of the fact that means are provided which make it possible to wet the working part—generally caused to vibrate transversely—over its entire surface with liquid that is fed via a small tube or catheter, completely surrounding the transmission part, which is caused to vibrate essentially longitudinally. Furthermore, owing to the fact that the catheter surrounding the transmission part consists of a material whose coefficient of friction relative to the liquid is negligible, it is possible to protect the transmission part against energy losses that would occur in particular on direct contact with the inner wall of the artery. Accordingly, there is no negative feedback to the transmission part and hence to the working part of the probe due to transmission of vibrations or formation of vibration nodes.

If the working part of the probe is angled relative to the longitudinal axis of the transmission part—the specific design of the working part depending on the required treatment, such as type and lumen of the artery and the extent of the plaque—access to the interior of the artery is simplified.

A spatulate working part is suitable for removing plaques extending over a small area, which may be carried out from two incisions in the artery, which are made distally and proximally. A working part of this type is also used for dissection of the distal, so-called "end-point," where the media is detached from the adventitia, after which a probe having a different form can be introduced through a small incision in the artery. Such a probe, the working part of which is in the form of a ring, but the transmission part is in the form of a long thin rod resembling the ring stripper known from the classical, half-open endarterectomy, proves to be advantageous for removing extensive obliterations, for example, in the femoral artery.

As already described at the outset, basically similar embodiments of such probes for use in classical endarterectomy and also probes, which operate with ultrasound are known. However, both in classical endarterectomy and in the removal of plaque with the aid of ultrasound by means of a probe of the type described in Austrian Patent No. 340,572, traumatic effects as well as incomplete removal of the atherosclerotically damaged media cannot be ruled out.

In comparison, the probe according to the invention is distinguished by the fact that it permits detachment of the occlusion region along the entire length of the artery with gentle, i.e. non-traumatic, and complete detachment of the media from the adventitia (relatively low frequencies of about 30 KHz, for example, 20–29 KHz, are used), since, even when the probe is inserted far into the artery, the annular working part vibrates with essentially unchanged energy and frequency and at the same time is wet uniformly with liquid over its annular surface.

The working part of the probe (whether the probe is a spatula probe or a ring probe, for example), when formed at an angle relative to the transmission part of the probe, vibrates at least partly transversely. This differs from the transmission part, which vibrates longitudinally.

The transmission part of such a probe, referred to below as a ring probe, is preferably in the form of a thin steel rod having a diameter of about I mm and a length of up to 60 cm or more, so that it can be moved without resistance even in the case of slightly curved arteries. The catheter conveying the liquid and surrounding the transmission part is preferably formed from a plastic that is dimensionally stable but flexible over its longitudinal dimension, polytetrafluoroethylene (PTFE) being particularly suitable as said plastic owing to excellent, antiadhesive properties. This ensures both improved slidability of the probe in the intermediate space between detached media and adventitia and inert behavior with respect to vibrations that may be transmissible via the liquid.

To ensure that the annular working part of the ring probe is wetted with liquid over its entire annular surface, the liquid is applied via an annular orifice that is optionally detained by the diameter of the catheter itself. Since the liquid emerges under pressure from this orifice, it is distributed over the vibrating ring on both sides of the junction between the ring and the transmission part.

The probe with the spatulate working part, referred to below as spatula probe, can in principle resemble the ring probe with regard to the transmission part and catheter for the supply of the liquid. However, since this probe is used in general for the treatment of a region directly adjacent to the incision in the artery, the working part thereof exclusively being inserted into the artery, less attention must be paid to the question of the slidability of the catheter material and the rigidity and flexibility thereof. In addition, another possible material is, for example, a material such as polyvinyl chloride (PVC), which is simpler and cheaper to process while providing similarly advantageous properties with regard to the avoidance of energy losses.

The design of the working part in the form of a spatula is preferred because this simplifies the guidance between detached media and adventitia, but other embodiments are also possible, for example, a rod-like working part or one in the form of a fillister head. The liquid-conveying catheter can completely enclose the spatulate working part in the region of the transition to the transmission part, this being possible in particular when it is made of relatively soft material. In this case, at least two orifices which are arranged on both sides of the spatula should be provided for the outflow of the liquid, so that the liquid emerging under a certain pressure is distributed over the entire surface of the working part. Several orifices can be provided in the same way, in every case symmetrically around the circumference of the working part, which is of any form.

A treatment set that permits the rapid, treatment-specific change of the treatment probes during a treatment will simplify and optimize the course of the treatment in an advantageous manner.

BRIEF DESCRIPTION OF THE DRAWINGS

The invention will be described in detail with reference to the following drawings in which like reference numerals refer to like elements, and wherein:

FIG. 2 shows a probe suitable for introduction into the interior of an artery;

FIG. 3 shows a probe suitable for the removal of plaques covering a small area;

FIG. 3a shows the probe of FIG. 3, viewed from a different angle;

DETAILED DESCRIPTION OF PREFERRED EMBODIMENTS

Figure 1:
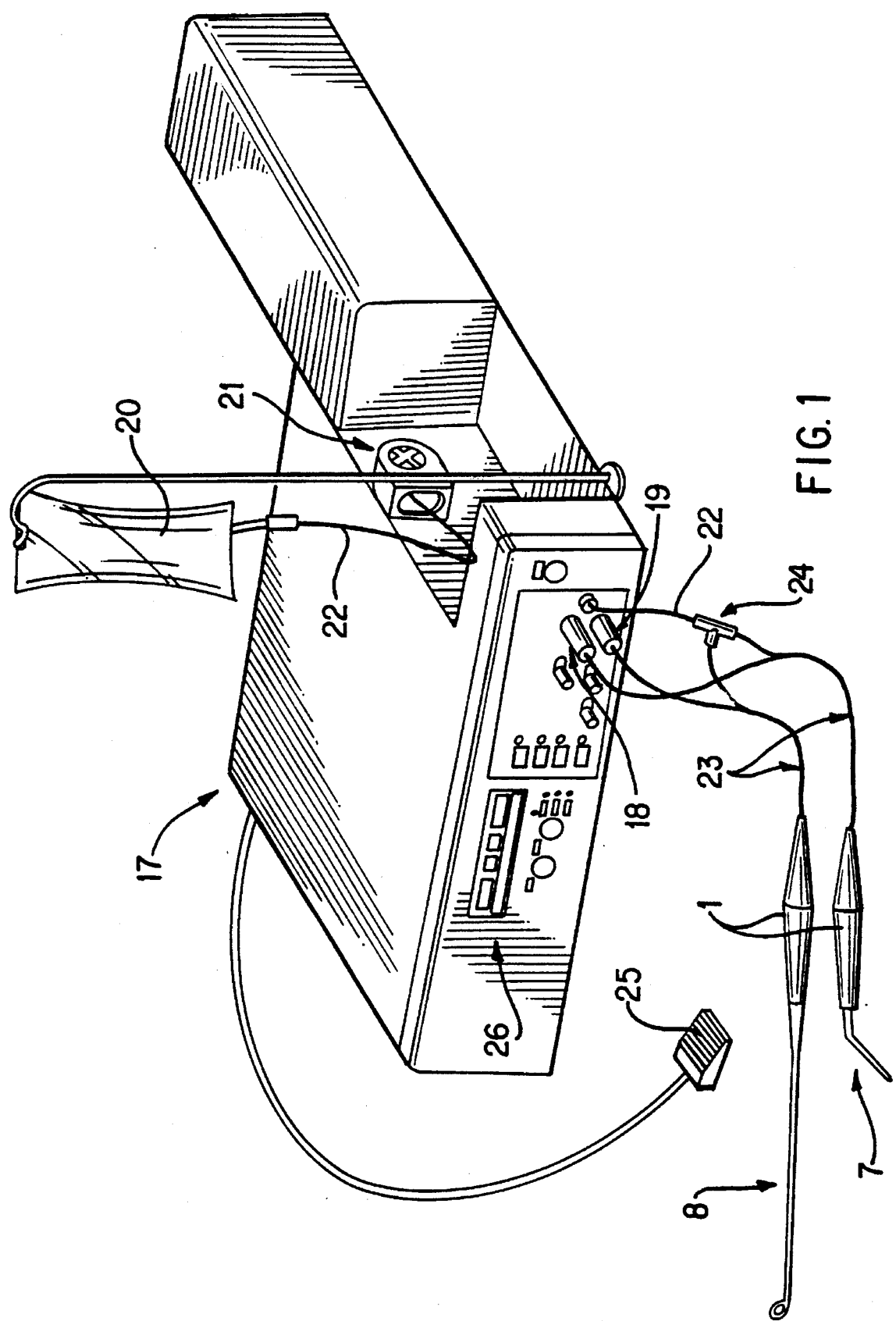
FIG. 1 shows an ultrasound generator to which two apparatus for the removal of atherosclerotic plaque are connected.

FIG. 1 shows an ultrasound generator 17 having two connections 18, 19, to which two apparatus according to the invention for the removal of atherosclerotic plaques are connected via lines 23. The two apparatus carry, on their particular handles 1, probes 7 and 8 of different embodiments, as is more clearly visible in FIG. 2 or FIG. 3 and FIG. 3a and whose specific use is described with reference to FIGS. 4a to 4l. Piezoelectric ultrasound transducers that are excited via the output signals of the generator with appropriate frequency and power (as controlled by an amplitude transformer (not shown) provided in the housing) are provided in the handles 1.

Sterile liquid is passed from a liquid container 20 by means of a peristaltic pump 21 and via a liquid line 22 to liquid channels 2 provided in the particular handles 1 of the two apparatus (FIGS. 2 and 3). A T-valve 24 is provided for passing the liquid to the probe which is presently in use. Liquid lines 22 and lines 23 have common sections.

The particular apparatus to be used can be selected by means of a pedal switch 25, and the liquid feed can be started by activating the pump 21. All necessary data, such as selected apparatus, ultrasonic frequency or duration of the treatment, are shown on a display 26.

Figure 5:
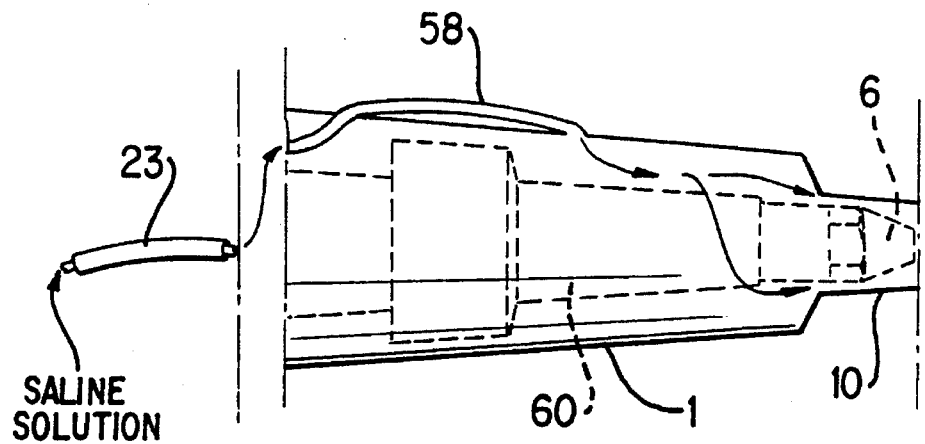
FIG. 5 shows an embodiment in which the ultrasonic transducer is provided in the handpiece, and a small tube is used so that the supplied liquid does not pass through the transducer, but instead bypasses it.
Figure 6:
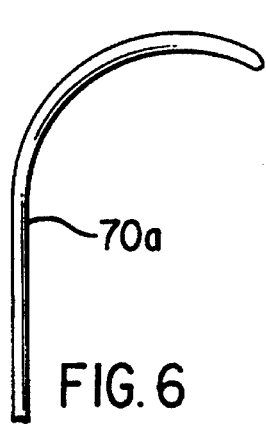
FIGS. 6–11B show possible tool structures, with FIGS. 10B and 11B being side views of the tools shown in FIGS. 10A and 11A, respectively.
Figure 7:
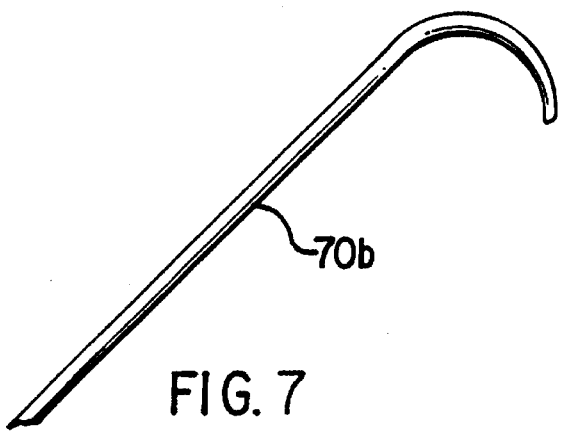
Figure 8:
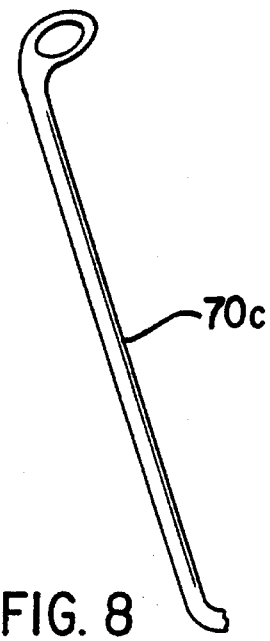
Figure 9:
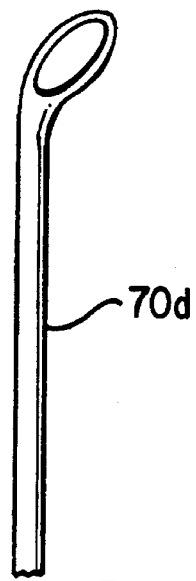
Figure 10A:
Figure 10B:
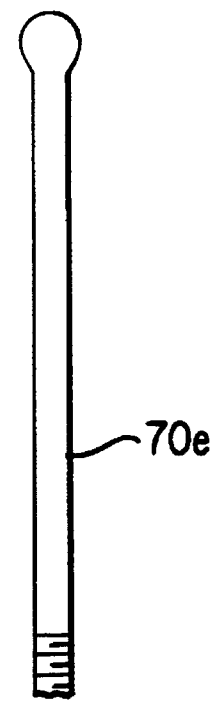
Figure 11A:
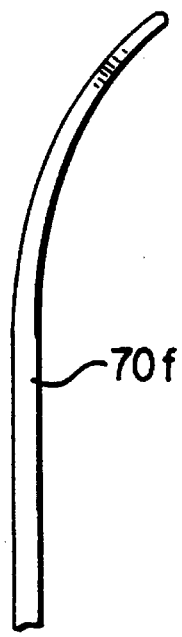
Figure 11B:
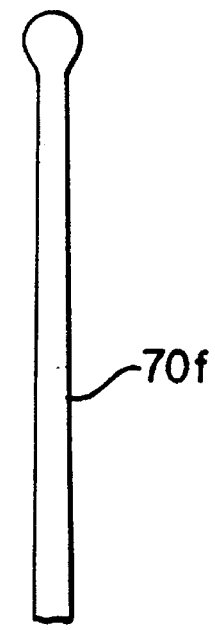

FIG. 2 shows the probe 8 that is suitable for insertion into an incision made in an artery. Such a probe 8 is referred to below as a ring probe because a so-called working part 4 in the form of a ring is attached to a long, rod-like transmission part 6, at a slight angle relative to the longitudinal axis 13 of the transmission part 6. The transmission part 6 is attached to the handle 1 that holds the ultrasound transducer and in whose interior the channel 2 may be provided for the sterile liquid, which is forced therefrom out of an orifice 27 into the interior of a space which is defined by a catheter 10 surrounding the transmission part 6. As an alternative to locating the liquid transmission channel 2 in the handle having the ultrasound transducer, the liquid supplied through tube 23 can be fed into a small tube 58 (see FIG. 5) that bypasses the ultrasound transducer 60 (instead of passing through it). Small tube 58 then supplies the liquid to the catheter 10 that surrounds the transmission part 6. Thus arrangement further prevents any possible attenuation of the ultrasonic energy supplied by transducer 60.

The catheter 10 is constructed of plastic that is essentially strong but flexible in the longitudinal dimension of the probe 8. Preferably the plastic of catheter 10 is PTFE, which, in addition to these properties, has particularly good slidability. This is made clear with reference to the procedure described in FIGS. 4a to 4l.

The catheter is open at its end facing the working part 4, so that the liquid which is forced by means of the pump 21 (FIG. 1) into the channel 2 emerges from this circular orifice 15 under a certain pressure and hence wets the annular working part on all sides. The working part 4 executes essentially transverse vibrations, cavitation cavities form in the liquid, and pressures of 2 to 3 atmospheres are generated when these cavities collapse and act on the surrounding material. Depending on the internal diameter of the artery, such ring probes 8 will have ring diameters of different magnitudes.

FIGS. 3 and 3a show a short probe 7 that is suitable for removing plaques covering a small area and in particular for the dissection of the so-called "end-point" and of the "proximal point" (to be described below). The working part 3 of this probe 7 is spatulate, and a region of the transmission part 5 is bent relative to the axis 14 defined by the common axis of handle I and the connected transmission part. The transmission part 5 is completely surrounded by a liquid-conveying catheter 9. As in the case of the ring probe 8 (FIG. 2), the liquid is forced by means of the pump 21 (FIG. 1) via the channel 2 in the handle 1 out of the orifice 27 into the intermediate space between catheter 9 and transmission part 5. The spatulate working part 3 projects freely from the catheter 9, which rests tightly against the probe 7 in this region of the transition between working part 3 and transmission part 5. Two orifices 16 (detail A in FIG. 3a) are provided on both sides of the spatulate working part 3. Liquid under pressure is forced through orifices 16 to the working part 3 so that—even in the case of a vibrating working part—there can be no immediate spraying of the liquid in the region of the orifice or orifices (as is the case, for example, in Austrian Patent No. 340,572), and the working part is wet uniformly on all sides.

Such a short probe optionally also can be of a different form, depending on the required use. As in the case of the ring probe, the transmission part can be straight and the working part can be, for example, rod-like or in the form of a fillister head. The type and number of orifices for the emergence of the liquid from the catheter 9 also is to be chosen accordingly. It is preferable that the orifices are arranged essentially symmetrically around the circumference of the working part.

FIGS. 6–11B show the working parts of tools 70a–70f that can be used with the invention. As can be appreciated from the drawings: tools 70e and 70f have a curved profile; tools 70a and 70b have profiles represented by a segment of a curve; tools 70e and 70f are spatulate; tools 70c and 70d have closed eyelets or rings. The working part always is inclined relative to the axis of the transmission part at an angle between 0° and 90°, preferably between 35° and 45°, so that the working part vibrates transversely to the axis of the transmission part.

The catheter or tube 9 used with the so-called spatula probe 7 generally is not inserted into the interior of an artery; or only a small portion of catheter 9, associated with its working part 3, may be inserted into the artery as is evident from FIGS. 4a to 4l. Accordingly, catheter 9 preferably consists of plastic, for example PVC due to its advantageous properties, as detailed earlier.

The apparatus according to the invention can be used for disobliteration in a wide range of vessels, either in the case of coronary scleroses or in the case of atherosclerosis of the initial subclavicular region. The use of the apparatus according to the invention is described in FIGS. 4a to 4l, with reference to the disobliteration of a peripheral vessel, namely the femoral artery 31, which may have extensive atherosclerotic obliterations.

Figure 4A:
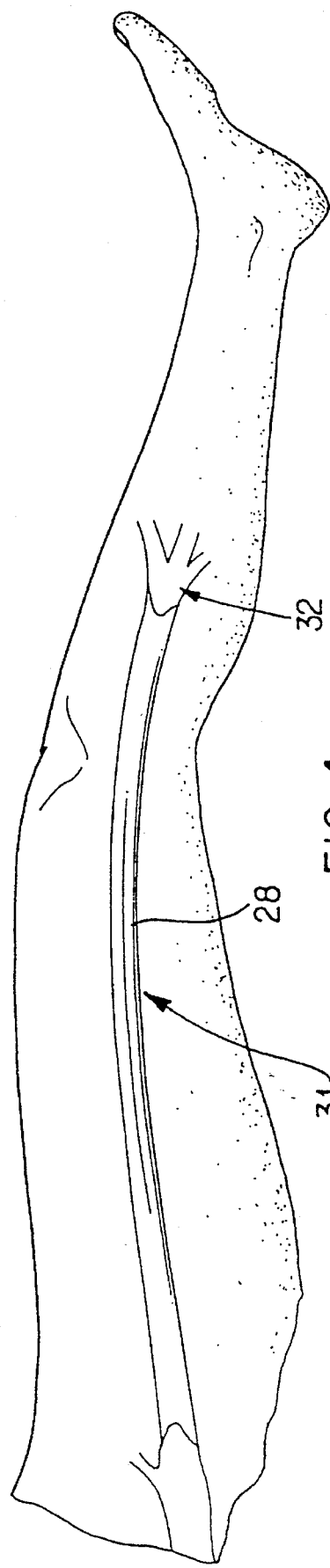
FIGS. 4a to 4l show successive steps of the process for the removal of an elongated occlusion in the femoral artery.
Figure 4C:
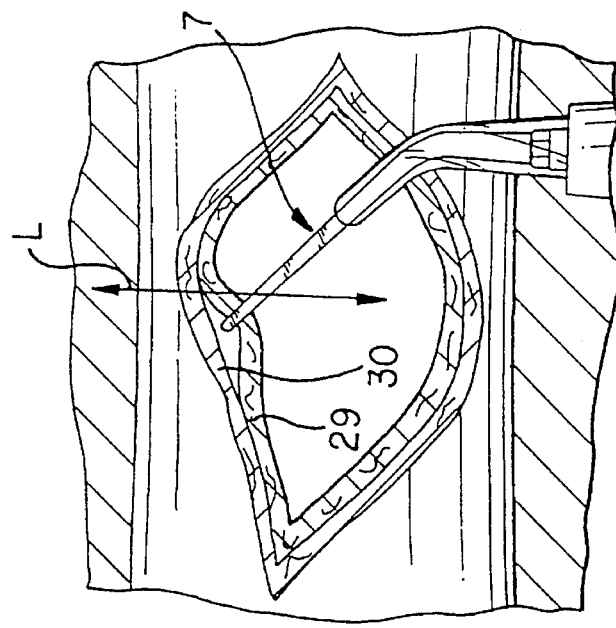
Figure 4B:
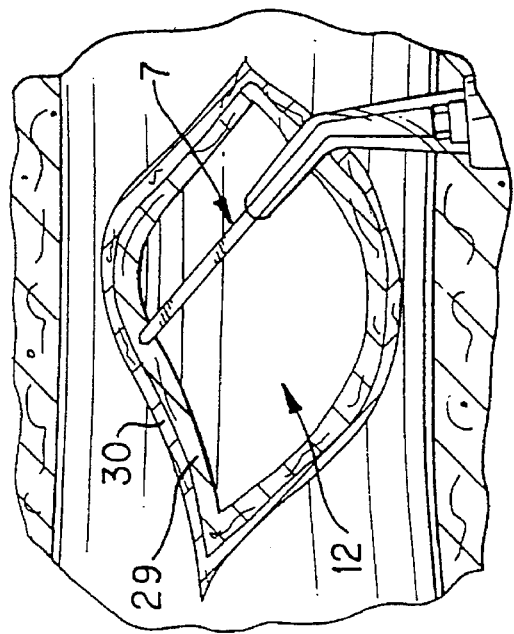

After the extent of the plaque obliteration 28 in the femoral artery 31 has been determined (FIG. 4a), for example by radiology, the artery 31 is exposed in the region of the so-called "end-point" 32 and an incision 12 is made (FIG. 4b). This incision 12 is about 1 to 1.5 cm long. In order to minimize the danger of postoperative thromboses, the dissection of the "end-point" 32 must be performed in such a way that the transition between treated and untreated inner wall of the artery is smooth, i.e. without projecting tissue pieces or tissue edges.

The incision 12 is in the region of the "endpoint" 32 and hence is at a point where there are no longer any plaque obliterations. The vibrating spatula probe 7, which vibrates generally in the direction L (FIG. 4c), is guided to the vessel wall (FIG. 4b) and, due to the cavitation pressure of about 2 to 3 atm. applied on the tissue, the media 29 becomes detached from the adventitia 30 because the connection between these two arterial wall layers is relatively weak (FIG. 4c). This relatively weak connection between the media, which is free of plaque, and the adventitia was precisely one of the causes in the previous methods for the partly coarsely irregular surfaces of the remaining inner wall of the artery that resulted upon dissection of the "end-point."

Figure 4D:
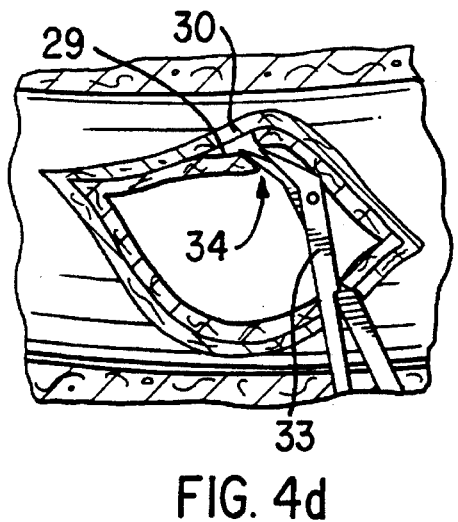
Figure 4E:
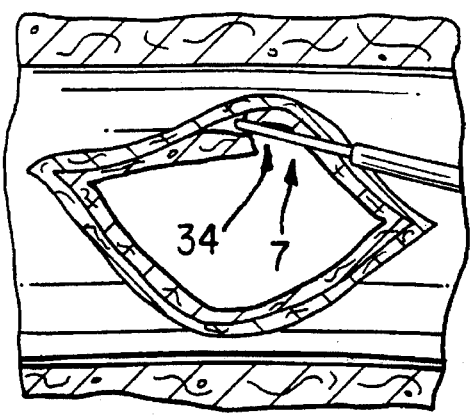

It should be noted that, simply by moving the rounded tip of vibrating spatula probe 7 towards the wall layer, the media 29 is detached—although only slightly—from the adventitia 30 (FIG. 4c), so that thereafter a transverse incision 34 about 0.5 to 1 mm long can be made in the media 29 by means of a small forceps 33 (FIG. 4d).

Figure 4F:
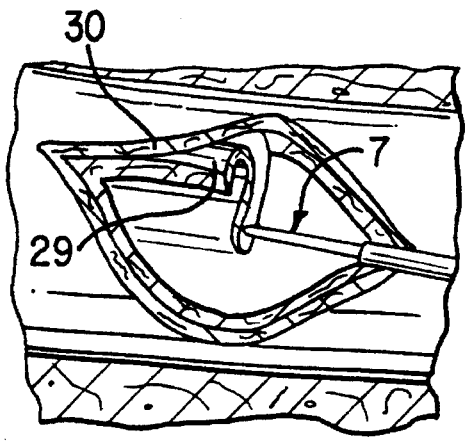
Figure 4G:
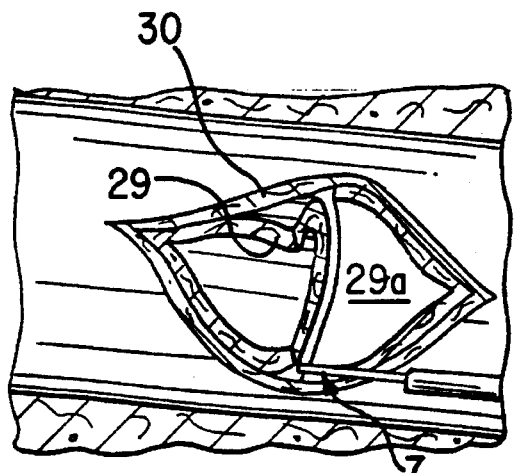

The round tip of the spatula probe 7 is inserted into this small transverse incision 34 (FIG. 4e) and is guided transversely around the inner wall of the artery (FIGS. 4f, 4g). Owing to the cavitational pressure, regular and smooth separation of the muscle fibers, which rest in a circular manner against the inner wall of the vessel, and of the intima takes place without a cut being made. Dissection of the "end-point" is thus achieved without other treatment steps, such as, optionally, the application of sutures to the interior of the artery. FIG. 4g shows the smooth separation between the media layer 29, detached from the adventitia 30, and the media layer 29a adhering to the adventitia 30.

Figure 4H:
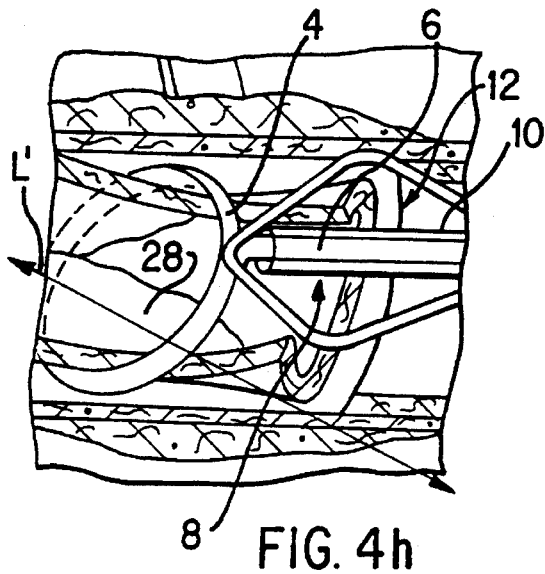
Figure 4I:
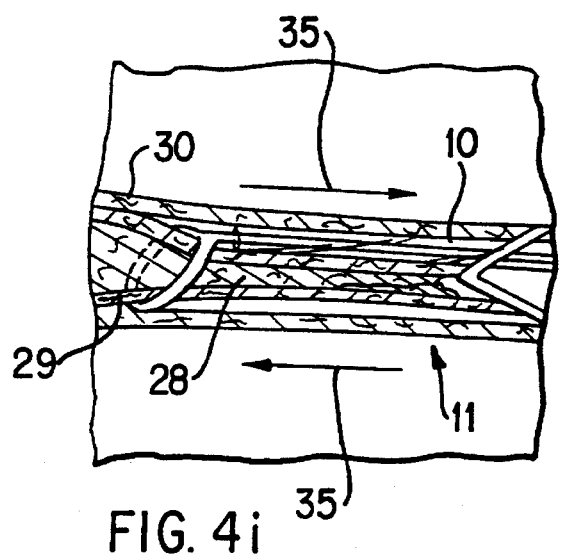

The second treatment phase relates to the total disobstruction of the cylinder occluding the artery. For this purpose, the ring probe 8 is inserted into the incision 12 so that the vibrating, annular working part 4, which vibrates generally in the direction L', is located between the detached media 29 and the adventitia 30 (FIG. 4h). The diameter of the ring 4 of the ring probe 8 is chosen according to the lumen of the artery. In the manner described above, i.e. at a pressure of 2 to 3 atm. on the tissue layers, the media 29 and hence also the obstructing plaque 28 become detached from the adventitia 30 without any traumatic effect on the vessel wall. Since the catheter 10 surrounding the vibrating transmission part 6 is constructed from a material having a low coefficient of friction, further advance of tool 8 within the artery 31 takes place without hindrance and the vibrational capacity of the transmission part 6 is not reduced or even eliminated as a result of pressure being applied to the transmission part 6 by the vessel wall (FIG. 4i). That is, unlike previous methods, the catheter 10 prevents the vessel wall from contacting the transmission part 6. Therefore vibration of the transmission part 6 and of the working part 4 is not reduced or otherwise damped. Additionally, the catheter 10 does not damp the transmission part 6. Catheter 10 is attached to the handle I so that vibrations are not transmitted to the catheter 10 from the ultrasound transducer. If the catheter 10 were vibrated, its vibration would be damped when it contacted the vessel wall, and this would also damp the working part.

Figure 4K:
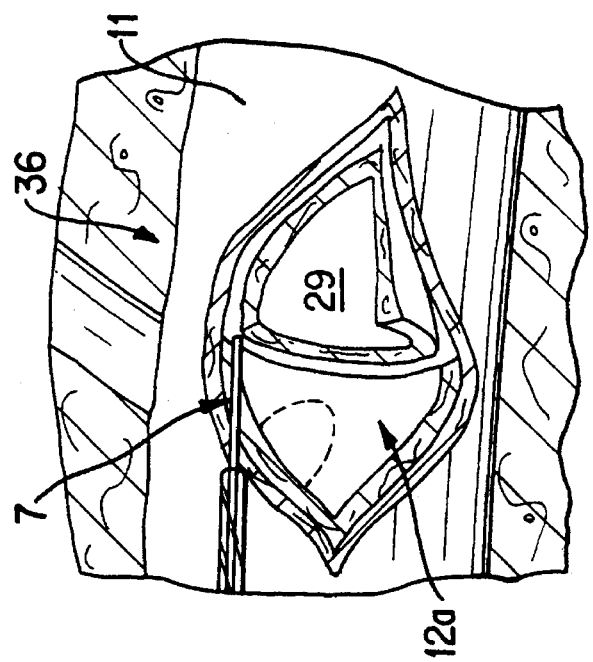
Figure 4J:
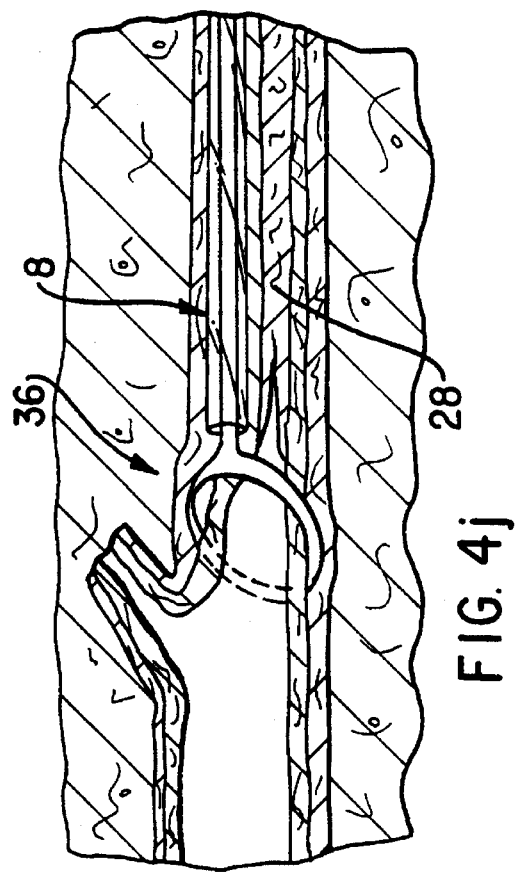

The second treatment step, in which the ring probe 8 is gently pushed forward and, if required, also backward, corresponding to the arrows 35 in FIG. 4i, ends at the "proximal point" 36, i.e. at a point of the artery which is once again free of occluding plaque 28 (FIG. 4j).

This "proximal point" 36 is now dissected using the spatula probe in a final treatment step in exactly the same way as "end-point" 32 was dissected. After withdrawal and removal of the ring probe 8 through the incision 12 at the "end-point" 32 (FIGS. 4a, 4b), an incision 12a is made in the longitudinal direction of the artery 31, the media 29 is first detached over a small area by means of the spatula probe 7, a small transverse incision is made in the detached media 29 in the manner described with reference to FIG. 4d and thereafter the vibrating spatula probe 7 is inserted and detachment of the media 29 from the adventitia 30 is effected by rotary movement of the probe (FIG. 4k). As in the case of the dissection of the "end-point," the separation line between detached and remaining media is crisp and smooth, and the danger of postoperative thromboses is minimized.

Figure 4L:
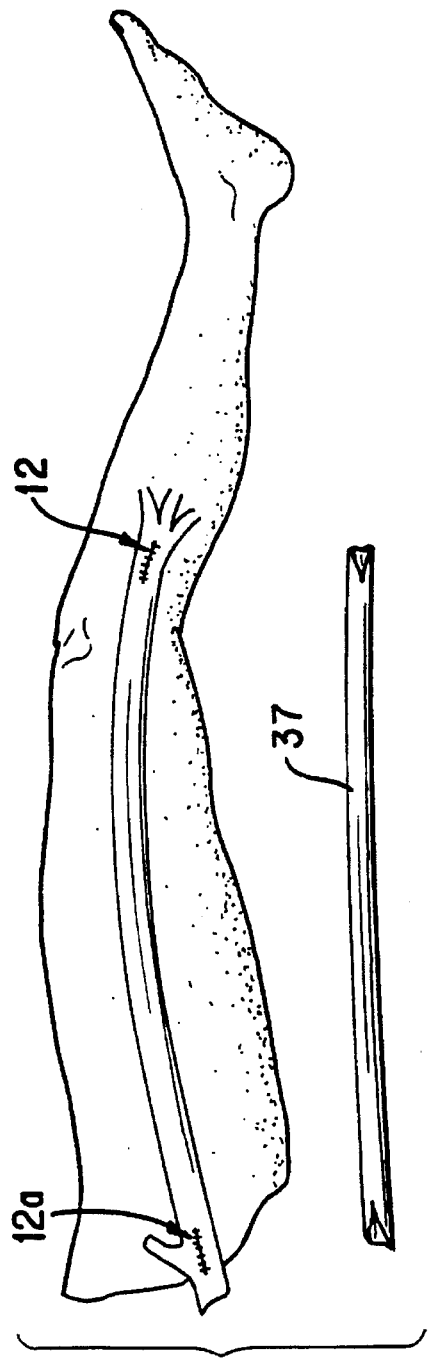

The entire occlusion cylinder 37 can be drawn through one of the two incisions 12 or 12a at the "endpoint" or at the "proximal point." The incisions 12 and 12a are sutured and the blood flow in the disobstructed artery region is reactivated (FIG. 4l).

The remaining inner wall of the disobstructed artery is free of irregularities because the entire media in this region has been removed, regardless of the particular degree of atherosclerosis. As detailed above, the invention has numerous advantages over previous techniques. The likelihood of thromboses forming at the end points is reduced because smooth transitions are formed at the "end point" and at the "proximal point." Additionally, the catheter 9, 10 precisely directs fluid to the entire working part of the tool, even when the working part is located deep inside a vessel. The catheter 10 also prevents the vessel wall from damping vibration of the tool.

When short regions of plaque are removed from vessels such as, for example, the carotid arteries, it usually is not necessary to use the ring-shaped tool 4. The same procedures detailed above are performed at the "end point" and at the "proximal point" at incisions 12, 12a. The spatula tool 7, however, can be used to detach the media and plaque from the adventitia between the incisions 12 and 12a.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. Apparatus for use in detaching atherosclerotic plaque from vessel walls by means of ultrasonic vibrations, comprising:

a handpiece including an ultrasonic frequency transducer;

a source of sterile liquid;

a probe having a transmission part attached to said handpiece and coupled to said ultrasonic transducer so that said probe is ultrasonically oscillated by said ultrasonic transducer, said probe including a working part insertable within vessel walls, the working part attached to the transmission part and extending from a longitudinal axis of the transmission part at an angle between 0° and 90° exclusive; and a liquid-conveying catheter completely surrounding the transmission part, a first end of said catheter attached to said source of liquid so that a second end of said catheter is capable of wetting all sides of the working part of the probe with liquid from the source of liquid, said handpiece including a liquid-conveying channel extending through said ultrasonic transducer, said channel having a first end in fluid communication with the source of sterile liquid and a second end attached to said first end of the catheter, wherein the catheter is made from a material having a negligible coefficient of friction relative to the liquid so that ultrasonic oscillation of the probe is not damped by said catheter or by a vessel wall when the probe and catheter are inserted into a vessel.

2. Apparatus according to claim 1, wherein the material of the catheter is polytetrafluoroethylene.

3. Apparatus according to claim 1, wherein said working part is in the form of a ring attached to one side of the transmission part and extending from the longitudinal axis of the transmission part at an angle between 0° and 90°.

4. Apparatus according to claim 1, wherein the working part is in the form of a spatula attached to the transmission part and extending from the longitudinal axis of the transmission part at an angle between 0° and 90°.

5. Apparatus according to claim 1, wherein the second end of the catheter includes at least one orifice for directing the liquid onto all portions of the working part.

6. Apparatus according to claim 5, wherein the second end of the catheter encloses the probe in a region of the probe between the working part and the transmission part, and wherein at least two orifices are provided at the second end of the catheter symmetrically on both sides of the working part.

7. Apparatus according to claim 1, wherein the transmission part and the catheter are flexible.

8. Apparatus according to claim 1, wherein the catheter is made of a plastic material.

9. Apparatus according to claim 8, wherein the plastic material is polyvinyl chloride.

10. Apparatus for use in detaching atherosclerotic plague from vessel walls by means of ultrasonic vibrations, comprising:

a handpiece including an ultrasonic frequency transducer;

a source of sterile liquid;

a probe having a transmission part attached to said handpiece and coupled to said ultrasonic transducer so that said probe is ultrasonically oscillated by said ultrasonic transducer, said probe including a working part insertable within vessel walls, the working part attached to the transmission part and extending from a longitudinal axis of the transmission part at an angle between 0° and 90° exclusive; and a liquid-conveying catheter completely surrounding the transmission part, a first end of said catheter connecting to said source of liquid so that a second end of said catheter is capable of wetting all sides of the working part of the probe with liquid from the source of liquid, wherein the catheter is made from a material having a negligible coefficient of friction relative to the liquid so that ultrasonic oscillation of the probe is not damped by said catheter or by a vessel wall when the probe and catheter are inserted into a vessel, wherein said working part and said transmission part are insertable within an incision made in an artery, said working part in the form of a ring attached to one end of the transmission part, said ring defining a plane extending at an angle between 0° and 90° from the longitudinal axis.

11. Apparatus according to claim 10, further comprising a liquid-conveying tube located outside of said handpiece and bypassing said ultrasonic frequency transducer, said tube having a first end in fluid communication with the source of liquid and a second end attached to said first end of the catheter.

12. Apparatus according to claim 10, wherein the material of the catheter is polytetrafluoroethylene.

13. Apparatus according to claim 10, wherein said handpiece includes a liquid-conveying channel extending through said ultrasonic transducer, said channel having a first end in fluid communication with the source of sterile liquid and a second end attached to said first end of the catheter.

14. Apparatus according to claim 10, further comprising a liquid-conveying tube located outside of said handpiece and bypassing said ultrasonic transducer, said tube having a first end in fluid communication with the source of sterile liquid and a second end attached to said first end of the catheter.

15. Apparatus according to claim 10, wherein the second end of the catheter includes at least one orifice for directing the liquid onto all portions of the working part.

16. Apparatus according to claim 10, wherein the transmission part and the catheter are flexible.

17. Apparatus according to claim 10, wherein the catheter is made of a plastic material.

18. Apparatus for use in detaching atherosclerotic plaque from vessel walls by means of ultrasonic vibrations, comprising:

a handpiece including an ultrasonic frequency transducer;

a source of sterile liquid;

a probe having a transmission part attached to said handpiece and coupled to said ultrasonic transducer so that said probe is ultrasonically oscillated by said ultrasonic transducer, said probe including a working part insertable within vessel walls, the working part attached to the transmission part and extending from a longitudinal axis of the transmission part at an angle between 0° and 90° exclusive; and a liquid-conveying catheter completely surrounding the transmission part, a first end of said catheter connecting to said source of liquid so that a second end of said catheter is capable of wetting all sides of the working part of the probe with liquid from the source of liquid, wherein the catheter is made from a material having a negligible coefficient of friction relative to the liquid so that ultrasonic oscillation of the probe is not damped by said catheter or by a vessel wall when the probe and catheter are inserted into a vessel, wherein said working part is in the form of a spatula insertable within an incision made in an artery, said working part extending from said longitudinal axis of the transmission part at an angle between 0° and 90°.

19. Apparatus according to claim 18, wherein the material of the catheter is polytetrafluoroethylene.

20. Apparatus according to claim 18, wherein said handpiece includes a liquid-conveying channel extending through said ultrasonic transducer, said channel having a first end in fluid communication with the source of sterile liquid and a second end attached to said first end of the catheter.

21. Apparatus according to claim 18, further comprising a liquid-conveying tube located outside of said handpiece and bypassing said ultrasonic transducer, said tube having a first end in fluid communication with the source of sterile liquid and a second end attached to said first end of the catheter.

22. Apparatus according to claim 18, wherein the second end of the catheter includes at least one orifice for directing the liquid onto all portions of the working part.

23. Apparatus according to claim 22, wherein the second end of the catheter encloses the probe in a region of the probe between the working part and the transmission part, and wherein at least two orifices are provided at the second end of the catheter symmetrically on both sides of the working part.

24. Apparatus according to claim 18, wherein the catheter is made of a plastic material.

25. Apparatus according to claim 24, wherein the plastic material is polyvinyl chloride.

26. Apparatus according to claim 18, further comprising a liquid-conveying tube located outside of said handpiece and bypassing said ultrasonic frequency transducer, said tube having a first end in fluid communication with the source of liquid and a second end attached to said first end of the catheter.

* * * * *